US012746187B2

(12) United States Patent
Hirano et al.

(10) Patent No.: US 12,746,187 B2
(45) Date of Patent: Sep. 29, 2026

(54) DENTAL IMPRESSION MATERIAL AND COMBINED IMPRESSION MATERIAL

(71) Applicant: GC Corporation, Shizuoka (JP)

(72) Inventors: Ayumu Hirano, Tokyo (JP); Yuki Shibuya, Tokyo (JP)

(73) Assignee: GC Corporation, Shizuoka (JP)

( * ) Notice: Subject to any disclaimer, the term of this patent is extended or adjusted under 35 U.S.C. 154(b) by 473 days.

(21) Appl. No.: 18/456,711

(22) Filed: Aug. 28, 2023

(65) Prior Publication Data

US 2024/0065946 A1 Feb. 29, 2024

(30) Foreign Application Priority Data

Aug. 31, 2022 (JP) ................................. 2022-138667

(51) Int. Cl.
*A61K 6/90* (2020.01)
*A61C 9/00* (2006.01)
*C08L 5/04* (2006.01)

(52) U.S. Cl.
CPC .............. *A61K 6/90* (2020.01); *A61C 9/0006* (2013.01); *C08L 5/04* (2013.01); *A61C 2201/00* (2013.01)

(58) Field of Classification Search
CPC .... A61K 6/90; A61C 9/0006; A61C 2201/00; C08B 37/0084
See application file for complete search history.

(56) References Cited

U.S. PATENT DOCUMENTS

| | | | | |
|---|---|---|---|---|
| 4,060,421 | A | 11/1977 | Yoshikawa et al. | |
| 9,597,350 | B2 * | 3/2017 | Larsen | A61K 31/734 |
| 2013/0032058 | A1 | 2/2013 | Gyakushi et al. | |
| 2013/0220172 | A1 | 8/2013 | Nagasawa et al. | |
| 2019/0076336 | A1 | 3/2019 | Usuki et al. | |
| 2022/0339081 | A1 | 10/2022 | Nakashima et al. | |
| 2024/0315931 | A1 * | 9/2024 | Niizeki | A61K 6/90 |

FOREIGN PATENT DOCUMENTS

| | | | |
|---|---|---|---|
| CN | 102811696 | 12/2012 | |
| EP | 4082512 | 11/2022 | |
| JP | S52-073591 | 6/1977 | |
| JP | H5-17315 | 1/1993 | |
| JP | H07-112910 | 5/1995 | |
| JP | H10-316521 | 12/1998 | |
| JP | 2007105018 A * | 4/2007 | |
| JP | 2014-94913 | 5/2014 | |
| JP | 2014-172891 | 9/2014 | |
| WO | 2012/063618 | 5/2012 | |
| WO | 2014/050028 | 4/2014 | |
| WO | 2017/163491 | 9/2017 | |
| WO | 2021/075095 | 4/2021 | |
| WO | 2021/131291 | 7/2021 | |
| WO | WO-2023053790 A1 * | 4/2023 | C08B 37/0084 |

OTHER PUBLICATIONS

Machine English translation of Seko Yoshinori, JP-2007105018-A, Apr. 26, 2007. (Year: 2007).*
Machine English translation of Matshshige et al., JP 2014172891A, Sep. 22, 2014. (Year: 2014).*
Capron Isabelle et al: "Water in water emulsions: phase separation and rheology of biopolymer solutions", Rheol. Acta, vol. 40 Sep. 1, 2001(Sep. 1, 2001) pp. 441-456, XP093122860, DOI: https://doi/org/10.1007/s003970100161 Retrieved from the Internet: URL:https://link.springer.com/article/10.1007/s003970100161 [retrieved on Jan. 23, 2024] p. 444, col. 2—p. 445, col. 1; figure 4.
Kimica Corporation, "Sodium alginate", Web Archiving around the World: National Diet Library Web Archiving Project (WARP), Nov. 23, 2019, http://web.archive.org/web/20191123002026/https://www.kimica.jp/products/NaAlgin/.
International Search Report for PCT/JP2022/031832 mailed on Oct. 25, 2022.

* cited by examiner

*Primary Examiner* — Coris Fung
*Assistant Examiner* — Caroline D. Liott
(74) *Attorney, Agent, or Firm* — IPUSA, PLLC

(57) ABSTRACT

A dental impression material includes: a base material paste that includes an alginate and water; and a curing material paste that includes a gelling reagent and a poorly water-soluble liquid compound. A viscosity of 10% aqueous solution of the alginate at 20° C. is 5 mPa·s or more and 90 mPa·s or less.

1 Claim, No Drawings

DENTAL IMPRESSION MATERIAL AND COMBINED IMPRESSION MATERIAL

CROSS-REFERENCE TO RELATED APPLICATIONS

This patent application is based on and claims priority to Japanese Patent Application No. 2022-138667 filed on Aug. 31, 2022, the entire contents of which are incorporated herein by reference.

TECHNICAL FIELD

The present invention relates to a dental impression material and a combined impression material.

BACKGROUND ART

In dentistry, a combined impression method is used to obtain an impression of the oral cavity when preparing a prosthesis. In the combined impression method, a first impression material with high fluidity is applied to the tooth, and then a second impression material with low fluidity is applied, and the first impression material and the second impression material are joined and combined with each other to obtain a highly accurate impression.

Conventionally, the agar-alginate combined impression method is known as the combined impression method (see, for example, Patent Document 1). In the agar-alginate combined impression method, an agar impression material with high fluidity and an alginate impression material with low fluidity are used as the combined impression material.

RELATED-ART DOCUMENTS

Patent Documents

[Patent Document 1] Japanese Examined Patent Publication No. S56-20019

SUMMARY OF THE INVENTION

Problems to be Solved by the Invention

However, because the fluidity of the agar impression material depends on temperature, complicated operations such as heat dissolution, heat retention, temperature adjustment, and the like are essential, resulting in low operability.

An object of the present invention is to provide a dental impression material that is excellent in operability and prevents adhesion to tooth surfaces.

Means for Solving the Problem

One aspect of the present invention is a dental impression material including: a base material paste that includes an alginate and water; and a curing material paste that includes a gelling reagent and a poorly water-soluble liquid compound. A viscosity of 10% aqueous solution of the alginate at 20° C. is 5 mPa·s or more and 90 mPa·s or less.

Effects of the Invention

According to one aspect of the present invention, a dental impression material that is excellent in operability and prevents adhesion to tooth surfaces can be provided.

DETAILED DESCRIPTION OF THE INVENTION

Hereinafter, embodiments for carrying out the present invention will be described.

<Dental Impression Material>

The dental impression material according to the present embodiment is used for the combined impression method. For example, the dental impression material according to the present embodiment may be combined with another alginate impression material to make a combined impression.

The dental impression material according to the present embodiment includes a base material paste and a curing material paste. In the present specification, the base material paste is a pasty base material. The curing material paste is a material that is mixed into the base material paste to cure the dental impression material.

[Base Material Paste]

The base material paste includes an alginate and water.

The alginate includes an alginate in which a viscosity of at least 10% aqueous solution of the alginate at 20° C. is 5 mPa·s or more and 90 mPa·s or less (hereinafter referred to as a first alginate). The viscosity of the 10% aqueous solution of the first alginate at 20° C. is preferably 10 mPa·s or more and 70 mPa·s or less, and more preferably 20 mPa·s or more and 50 mPa·s or less.

When the viscosity of the 10% aqueous solution of the first alginate at 20° C. is 5 mPa·s or more, the viscosity of the base material paste does not decrease too much. Accordingly, it is possible to prevent the deterioration in the operability of the dental impression material. When the viscosity of the 10% aqueous solution of the first alginate at 20° C. is 90 mPa·s or less, the fluidity of the mixture of the base material paste and the curing material paste is higher. Accordingly, it is possible to improve the accuracy of the impression when the dental impression material according to the present embodiment is combined with another alginate impression material to make a combined impression.

Examples of the first alginate include alkali metal alginates such as sodium alginate and potassium alginate, ammonium alginates such as ammonium alginate and triethanolamine alginate, and the like. Two or more types of the alginates may be used in combination. Among them, alkali metal alginates are preferable, and sodium alginate and potassium alginate are more preferable, because of their availability; ease of handling; physical properties of the cured body of the dental impression material; and so on.

The content of the first alginate in the base material paste is preferably 1 mass % or more and 20 mass % or less, more preferably 3 mass % or more and 15 mass % or less, and even more preferably 5 mass % or more and 10 mass % or less.

When the content of the first alginate in the base material paste is 1 mass % or more, the content of the alginate in the base material paste is increased while minimizing the increase in viscosity.

Accordingly, it is possible to prevent the adhesion to the tooth surface while maintaining the operability of the dental impression material. When the content of the first alginate is 20 mass % or less, the viscosity of the dental impression material does not become too high. Accordingly, it is possible to prevent the deterioration in the accuracy of the impression when the dental impression material is combined with another alginate impression material to make a combined impression.

The viscosity of the 1% aqueous solution of the first alginate at 20° C. is preferably 2 mPa·s or less, more preferably 1.5 mPa·s or less, and even more preferably 1 mPa·s or less.

When the viscosity of the 1% aqueous solution of the first alginate at 20° C. is 2 mPa·s or less, even when the amount of alginate contained in the dental impression material is increased, the increase in the viscosity of the dental impression material is reliably minimized. Accordingly, it is possible to prevent the adhesion to the tooth surface while preventing the deterioration in the accuracy of the impression.

The lower limit of the viscosity of the 1% aqueous solution of the first alginate at 20° C. is not limited, but preferably 0.1 mPa·s or more, from the viewpoint of preventing the deterioration in the accuracy of the impression due to too low viscosity of the dental impression material.

In the present embodiment, an alginate other than the first alginate described above (hereinafter referred to as a second alginate) may be included.

The viscosity of a 10% aqueous solution of the second alginate at 20° C. is preferably more than 90 mPa·s and 1,000 mPa·s or less, more preferably 95 mPa·s or more and 700 mPa·s or less, and even more preferably 100 mPa·s or more and 500 mPa·s or less.

When the viscosity of the 10% aqueous solution of the second alginate at 20° C. is more than 90 mPa·s, the impression becomes less likely to be damaged when the dental impression material is combined with another alginate impression material to make a combined impression. When the viscosity of the 10% aqueous solution of the second alginate at 20° C. is 1,000 mPa·s or less, the fluidity of the mixture of the base material paste and the curing material paste is higher. Accordingly, it is possible to improve the accuracy of the impression when the dental impression material according to the present embodiment is combined with another alginate impression material to make a combined impression.

Examples of the second alginate include alkali metal alginates such as sodium alginate and potassium alginate, ammonium alginates such as ammonium alginate and triethanolamine alginate, and the like. Two or more types of the alginates may be used in combination. Among them, alkali metal alginates are preferable, and sodium alginate and potassium alginate are more preferable, because of their availability, ease of handling, and physical properties of the cured body of the dental impression material.

The content of the second alginate in the base material paste is preferably 1 mass % or more and 20 mass % or less, more preferably 3 mass % or more and 15 mass % or less, and even more preferably 5 mass % or more and 10 mass % or less.

When the content of the second alginate in the base material paste is 1 mass % or more, the fluidity does not become too low when the dental impression material according to the present embodiment is combined with another alginate impression material to make a combined impression. Accordingly, it is possible to improve the accuracy of the impression. When the content of the second alginate in the base material paste is 20 mass % or less, the fluidity does not become too high when the dental impression material according to the present embodiment is combined with another alginate impression material to make a combined impression. Accordingly, it is possible to improve the accuracy of the impression.

The mass ratio of the content of the second alginate to the content of the first alginate is preferably 0.4 or more and 2.0 or less, more preferably 0.5 or more and 1.9 or less, and 0.6 or more and 1.8 or less. When the mass ratio of the content of the second alginate to the content of the first alginate is 0.4 or more and 2.0 or less, it is possible to prevent the adhesion of the dental impression material to the tooth surface while minimizing the decrease in the fluidity of the mixture of the base material paste and the curing material paste.

The content of the whole alginate (the first alginate and the second alginate) in the base material paste is preferably 6 mass % or more and 20 mass % or less, more preferably 8 mass % or more and 18 mass % or less, and even more preferably 10 mass % or more and 16 mass % or less.

When the content of the whole alginate in the base material paste is 6 mass % or more, the content of the alginate in the dental impression material is higher. Accordingly, the impression is less likely to be damaged when the dental impression material is combined with another alginate impression material to make a combined impression, and the cured body of the dental impression material is less likely to adhere to the tooth surface. When the content of the whole alginate in the base material paste is 20 mass % or less, the content of the alginate in the dental impression material does not increase too much when the dental impression material is combined with another alginate impression material to make a combined impression. Accordingly, it is possible to improve the accuracy of the impression.

As the water, for example, ion-exchange water, distilled water, and the like may be used, and water sterilized with sodium hypochlorite or the like may be used.

The content of water in the base material paste is preferably 70 mass % or more and 99 mass % or less, more preferably 75 mass % or more and 95 mass % or less, and even more preferably 80 mass % or more and 90 mass % or less.

The content of water in the dental impression material is preferably 35 mass % or more and 90 mass % or less, more preferably 40 mass % or more and 80 mass % or less, even more preferably 55 mass % or more and 75 mass %, and even more preferably 45 mass % or more and 70 mass %.

Preferably, the base material paste further contains a curing retarder and the like. Accordingly, the time available to operate the dental impression material according to the present embodiment is extended.

Examples of the curing retarder include phosphates such as trisodium phosphate and tripotassium phosphate, and condensed phosphates such as sodium pyrophosphate and potassium pyrophosphate, and the like. Two or more compounds may be used in combination.

The content of the curing retarder in the base material paste is preferably 0.01 mass % or more and 10 mass % or less, more preferably 0.05 mass % or more and 5 mass % or less, and even more preferably 0.1 mass % or more and 3 mass % or less.

When the content of the curing retarder in the base material paste is 0.01 mass % or more, the time available to operate the dental impression material according to the present embodiment is extended. When the content of the curing retarder in the base material paste 10 mass % or less, the initial curing time of the dental impression material according to the present embodiment is shortened, and the strength of the cured body of the dental impression material according to the present embodiment is improved.

The base material paste may further contain fillers, colorants, preservatives, disinfectants, fragrances, pH adjusters, surfactants, and the like.

The consistency of the base material paste is preferably 30 mm or more. When the consistency of the base material paste is 30 mm or more, the fluidity of the mixture of the base material paste and the curing material paste is higher. Therefore, it is possible to improve the accuracy of the impression when the dental impression material according to the present embodiment is combined with another alginate impression material to make a combined impression.

[Curing Material Paste]

The curing material paste includes a gelling reagent and a poorly water-soluble liquid compound.

As the gelling reagent, a compound of divalent or more metals may be used.

Examples of the compound of divalent or more metals include salts, oxides, hydroxides, and the like of the divalent or more metals. Two or more compounds may be used in combination.

Examples of the divalent or more metals include calcium, magnesium, zinc, aluminum, iron, titanium, zirconium, tin, and the like.

Examples of the salts of the divalent or more metals include calcium sulfate dihydrate ($CaSO_4 \cdot 2H_2O$), calcium sulfate hemihydrate ($CaSO_4 \cdot 1/2H_2O$), anhydrous calcium sulfate ($CaSO_4$), and the like.

Examples of the oxides of the divalent or more metals include calcium oxide, magnesium oxide, zinc oxide, titanium oxide, zirconium oxide, tin oxide, and the like.

Examples of the hydroxides of the divalent or more metals include calcium hydroxide, magnesium hydroxide, zinc hydroxide, aluminum hydroxide, iron hydroxide, and the like.

The content of the gelling reagent in the curing material paste is preferably 10 mass % or more and 60 mass % or less. When the content of the gelling reagent in the curing material paste is 10 mass % or more, the strength of the cured body of the dental impression material according to the present embodiment is improved. When the content of the gelling reagent in the curing material paste is 60 mass % or less, the time available to operate the dental impression material according to the present embodiment is extended.

The poorly water-soluble liquid compound is not limited as long as it is possible to make a paste of the gelling reagent, but may be, for example, hydrocarbon compounds, aliphatic alcohols, aromatic alcohols, fatty acids, fatty acid esters, silicone oils, and the like. Two or more compounds may be used in combination.

In the present specification, poorly water-soluble means that the solubility in 100 g of water at 20° C. is 5 g or less.

The hydrocarbon compound may be either a chain compound or a cyclic compound.

Examples of the hydrocarbon compound include hexane, heptane, octane, nonane, decane, undecane, dodecane, tridecane, tetradecane, pentadecane, 2,7-dimethyloctane, 1-octene, cycloheptane, cyclononane, kerosene, liquid paraffin, and the like.

The aliphatic alcohol may be either a saturated aliphatic alcohol or an unsaturated aliphatic alcohol.

Examples of the aliphatic alcohol include 1-hexanol, 1-octanol, citronellol, oleyl alcohol, and the like.

Examples of the aromatic alcohol include benzyl alcohol, m-cresol, and the like.

The fatty acid may be either a saturated fatty acid or an unsaturated fatty acid.

Examples of the fatty acid include hexanoic acid, octanoic acid, oleic acid, linoleic acid, and the like.

The fatty acid ester may be either a saturated fatty acid ester or an unsaturated fatty acid ester.

Examples of the fatty acid ester include ethyl octanoate, butyl phthalate, glyceride oleate, olive oil, sesame oil, liver oil, whale oil, and the like.

Examples of the silicone oil include polydimethylsiloxane, polymethylphenylsiloxane, polymethylhydrogensiloxane, polyphenylhydrogensiloxane, and the like.

The content of the poorly water-soluble liquid compound in the curing material paste is preferably 10 mass % or more and 50 mass % or less, more preferably 15 mass % or more and 30 mass % or less. When the content of the poorly water-soluble liquid compound in the curing material paste is 10 mass % or more, the operability of the dental impression material according to the present embodiment is improved. When the content of the poorly water-soluble liquid compound in the curing material paste is 50 mass % or less, the strength of the cured body of the dental impression material according to the present embodiment is improved.

The curing material paste preferably further contains polybutene. Accordingly, the curing property of the dental impression material according to the present embodiment is improved, and the time available to operate the dental impression material according to the present embodiment is extended.

The polybutene is preferably liquid.

The polybutene may be synthesized by copolymerizing isobutene and 1-butene.

The number average molecular weight of the polybutene is preferably 300 or more and 4,000 or less.

The content of the polybutene in the curing material paste is preferably 0.5 mass % or more and 30 mass % or less, more preferably 1 mass % or more and 20 mass % or less. When the content of the polybutene in the curing material paste is 0.5 mass % or more and 30 mass % or less, the operability of the dental impression material according to the present embodiment is improved.

The curing material paste preferably further contains a curing retarder. Accordingly, the time available to operate the dental impression material according to the present embodiment is extended.

Examples of the curing retarder include phosphates such as trisodium phosphate and tripotassium phosphate, condensed phosphates such as sodium pyrophosphate and potassium pyrophosphate. Two or more compounds may be used in combination.

The content of the curing retarder in the curing material paste is preferably 0.01 mass % or more and 10 mass % or less. When the content of the curing retarder in the curing material paste is 0.01 mass % or more, the time available to operate the dental impression material according to the present embodiment is extended. When the content of the curing retarder in the curing material paste is 10 mass % or less, the initial curing time of the dental impression material according to the present embodiment is shortened, and the strength of the cured body of the dental impression material according to the present embodiment is improved.

The curing material paste may further contain fillers, curing modifiers, surfactants, colorants, preservatives, disinfectants, fragrances, pH adjusters, and the like.

Examples of materials constituting the filler include clay minerals such as diatomaceous earth, talc, and smectite, and inorganic oxides such as silica, alumina, and the like. Two or more materials may be used in combination.

Examples of the curing modifier include potassium titanium fluoride, potassium silicofluoride, and the like. Two or more compounds may be used in combination.

Examples of the surfactant include polyoxyethylene alkyl ether and the like. Two or more compounds may be used in combination.

The consistency of the curing material paste is preferably 30 mm or more. When the consistency of the curing material paste is 30 mm or more, the fluidity of the mixture of the base material paste and the curing material paste is higher. Accordingly, it is possible to improve the accuracy of the impression when the dental impression material according to the present embodiment is combined with another alginate impression material to make a combined impression.

The consistency of the mixture of the base material paste and the curing material paste is 36 mm or more, and preferably 38 mm or more. When the consistency of the mixture of the base material paste and the curing material paste is 36 mm or more, the fluidity of the mixture of the base material paste and the curing material paste is higher. Accordingly, it is possible to improve the accuracy of the impression when the dental impression material according to the present embodiment is combined with another alginate impression material to make a combined impression.

The upper limit of the consistency of the mixture of the base material paste and the curing material paste is not particularly limited, but the upper limit is typically 50 mm.

The method of measuring the consistency of the mixture of the base material paste and the curing material paste is as follows. The base material paste and the curing material paste are mixed by hand under the condition of 23±2° C. until they become uniform. 0.5±0.2 ml of the mixture is placed on a glass plate. 30 seconds after the start of the mixing of the base material paste and the curing material paste, a weight is placed so that it weighs 500 g together with the glass plate. The weight is removed 5 seconds after the weight is placed. The dimensions of the largest and smallest sections between parallel cut lines of the spread mixture are measured in 0.5 mm increments. The average value of the dimensions of the largest and smallest sections between the parallel cut lines of the spread mixture is obtained to determine the consistency of the paste.

[Application of Dental Impression Material]

The dental impression material according to the present embodiment is used by mixing the base material paste and the curing material paste.

For example, a manual or electric extrusion device is used to extrude the base material paste and the curing material paste, which are loaded in separate packaging containers, and to pass the pastes through a nozzle. A mixture thus obtained is applied to the tooth.

Examples of the packaging container include molded resin or metal articles, resin or metal bags, and the like.

The mass ratio of the base material paste to the curing material paste when mixing the curing material paste and the base material paste is preferably 1 or more and 5 or less.

As a result of intense research, the inventors have found that by increasing the content of the alginate impression material in the base material paste that is included in the dental impression material, it is possible to obtain the effect of preventing the dental impression material from adhering to the tooth surface. On the other hand, when the content of the alginate impression material in the base material paste is increased, the viscosity of the base material paste becomes too high, and the base material paste and the curing material paste cannot be mixed.

To address this issue, in the present embodiment, the base material paste contains the alginate (first alginate) in which a viscosity of 10% aqueous solution of the alginate at 20° C. is 5 mPa·s or more and 90 mPa·s or less as described above. Accordingly, even when the amount of alginate contained in the dental impression material is increased, the increase in the viscosity of the dental impression material is minimized, which enables the mixing of the base material paste and the curing material paste. Therefore, the dental impression material according to the present embodiment is excellent in operability, allows for obtaining a highly accurate impression by combined impression with another alginate impression material, and prevents adhesion to the tooth surface.

Further, in the present embodiment, the viscosity of the 1% aqueous solution of the first alginate at 20° C. may be 2 mPa·s or less as described above. Accordingly, even when the amount of alginate contained in the dental impression material is increased, the increase in the viscosity of the dental impression material can be reliably minimized. Therefore, the dental impression material according to the present embodiment is more excellent in operability, allows for obtaining a more highly accurate impression by making a combined impression combined with another alginate impression material, and reliably prevents adhesion to the tooth surface.

<Combined Impression Material>

The combined impression material according to the present embodiment includes the dental impression material according to the present embodiment and the alginate impression material. That is, the dental impression material according to the present embodiment can be applied for the combined impression.

The alginate impression material is not particularly limited, but for example, an alginate impression material used for an agar-alginate combined impression method may be used.

The alginate impression material may be a powder type, or may be a paste type that includes a base material paste containing alginate and water, and a curing material paste containing a gelling reagent and a poorly water-soluble liquid compound.

The paste-type alginate impression material is the same as the dental impression material according to the present embodiment except that the alginate contained in the base material paste is an alginate in which a viscosity of 10% aqueous solution of the alginate at 20° C. is more than 90 mPa·s and 1,000 mPa·s or less.

When the combined impression material according to the present embodiment is used, the impression of the tooth can be obtained.

For example, after the dental impression material according to the present embodiment is applied to the tooth, the alginate impression material is applied to the tooth to which the dental impression material according to the present embodiment is applied.

The combined impression material according to the present embodiment includes the dental impression material according to the present embodiment and another alginate impression material as described above, that is, the dental impression material according to the present embodiment is applied for the combined impression. Accordingly, the same effect as the dental impression material according to the present embodiment can be obtained. In the present specification, another alginate impression material refers to an alginate impression material different from the dental impression material according to the present embodiment.

That is, in the combined impression material according to the present embodiment, the base material paste included in the dental impression material contains the alginate (first alginate) in which a viscosity of 10% aqueous solution of the alginate at 20° C. is 5 mPa·s or more and 90 mPa·s or less.

Accordingly, even when the amount of alginate contained in the dental impression material is increased, the increase in the viscosity of the dental impression material is minimized, which enables the mixing of the base material paste and the curing material paste. Therefore, the combined impression material according to the present embodiment is excellent in operability of the dental impression material, allows for obtaining a highly accurate impression by combined impression with another alginate impression material, and prevents adhesion to the tooth surface.

Example

Examples of the present invention are described below, but the invention is not limited to the examples. Examples and comparative examples were evaluated by the following tests. In the following, values without units are mass standards (parts by mass or mass %) unless otherwise noted.

<Preparation of Curing Material Paste>

45 parts by mass of anhydrous calcium sulfate ($CaSO_4$), 6 parts by mass of magnesium hydroxide, 2 parts by mass of zinc oxide, 23 parts by mass of liquid paraffin, 4 parts by mass of polybutene, 1.5 parts by mass of tripotassium phosphate, 12.5 parts by mass of silica, 3 parts by mass of potassium titanium fluoride, and 3 parts by mass of polyoxyethylene alkyl ether were mixed to obtain a curing material paste.

<Preparation of Base Material Paste>

Alkali metal salts of alginic acid, water, and sodium pyrophosphate were mixed in the formula (in parts by mass) presented in Table 1 to obtain a base material paste.

Details of the alkali metal salts of alginic acid are given below.

[First Alginate]

Sodium Alginate ULV-L3G (manufactured by Kimica Corporation): viscosity of 10% aqueous solution at 20° C. is 20 to 50 mPa·s, viscosity of 1% aqueous solution is 0.6 mPa·s Potassium Alginate K-ULV-L3G (manufactured by Kimica Corporation): viscosity of 10% aqueous solution at 20° C. is 20 to 50 mPa·s, viscosity of 1% aqueous solution is 0.5 mPa·s

[Second Alginate]

Potassium Alginate K-1G (manufactured by Kimica Corporation): viscosity of 1% aqueous solution at 20° C. is 100 to 200 mPa·s Sodium Alginate I-3G (manufactured by Kimica Corporation): viscosity of 1% aqueous solution at 20° C. is 300 to 400 mPa·s

[Adhesiveness]

A cross section of a bovine tooth embedded in acrylic resin were polished with #600 water-resistant abrasive paper. A mixture of a dental impression material was prepared by mixing the curing material paste and the base material paste at a mass ratio of 1:2 under the condition of 23±2° C. 1.5 ml of the prepared mixture of the dental impression material was extruded onto the surface of the cross section of the polished bovine tooth and pressed with an acrylic plate, thereby preparing a test piece. The test piece was placed in a thermostatic water bath at 35° C. to cure the mixture of the dental impression material. The test piece was taken out, the cured mixture was peeled off from the bovine teeth together with the acrylic plate, and the surface was observed. The results are presented in Tables 1 to 3.

[Evaluation Criteria]

Excellent: No attaching whatsoever

Good: Slightly attached

Poor: Fully attached

<Mixing Property with Curing Material Paste>

A cartridge was filled with the curing material paste and the base material paste at a mass ratio of 1:2 under the condition of 23±2° C., a mixture (mixed paste) of the dental impression material was extruded from the cartridge, and the mixed paste was visually observed. The results are presented in Table 1 to 3.

[Evaluation Criteria]

Excellent: Evenly mixed

Good: Mixable, but unevenness remained

Poor: Impossible to mix

<Consistency>

The curing material paste and the base material paste were mixed at a mass ratio of 1:2 under the condition of 23±2° C. 0.5±0.2 ml of the mixture of the base material paste and the curing material paste was then placed on a glass plate. 25 seconds after the start of the mixing of the base material paste and the curing material paste, a weight was placed so that a load of 14.71±0.01 N together with the glass plate was applied. The weight was removed 5 seconds after the weight was placed. The dimensions of the largest and smallest sections between parallel cut lines of the spread mixture were measured in units, and their average value was obtained. The consistency test was performed only for Examples 1, 2, 8, and 9, and Comparative Examples 2 and 3. The results are presented in Tables 1 and 3.

[Evaluation Criteria]

Excellent: Consistency was 38 mm or more

Good: Consistency was 36 mm or more and less than 38 mm

Poor: Consistency was less than 36 mm

TABLE 1

| ALGINATE | VISCOSITY (mPa · s) | EXAMPLE | | | | | |
|---|---|---|---|---|---|---|---|
| | | 1 | 2 | 3 | 4 | 5 | 6 |
| POTASSIUM ALGINATE K-1G | 100~200 (1% AQUEOUS SOLUTION) | 7 | 7 | 7 | 7 | 6.5 | 6 |
| SODIUM ALGINATE ULV-L3G | 20~50 (10% AQUEOUS SOLUTION) | 7 | 6 | 5 | 4 | 6.5 | 9 |
| POTASSIUM ALGINATE K-ULV-L3G | 20~50 (10% AQUEOUS SOLUTION) | | | | | | |
| SODIUM ALGINATE I-3G | 300~400 (1% AQUEOUS SOLUTION) | | | | | | |
| TOTAL ALGINATE | | 14 | 13 | 12 | 11 | 13 | 15 |

TABLE 1-continued

| ALGINATE | VISCOSITY (mPa · s) | EXAMPLE 1 | 2 | 3 | 4 | 5 | 6 |
|---|---|---|---|---|---|---|---|
| DISTILLED WATER | | 85.8 | 86.8 | 87.8 | 88.8 | 86.8 | 84.8 |
| SODIUM PYROPHOSPHATE | | 0.2 | 0.2 | 0.2 | 0.2 | 0.2 | 0.2 |
| TOTAL | | 100 | 100 | 100 | 100 | 100 | 100 |
| ADHESIVENESS | | EXCELLENT | EXCELLENT | GOOD | GOOD | GOOD | GOOD |
| MIXING PROPERTY WITH CURING MATERIAL PASTE | | EXCELLENT | EXCELLENT | EXCELLENT | EXCELLENT | EXCELLENT | EXCELLENT |
| CONSISTENCY (mm) | | 38.2 | 39.7 | | | | |

TABLE 2

| ALGINATE | VISCOSITY (mPa · s) | EXAMPLE 7 | 8 | 9 | 10 | 11 | 12 | 13 |
|---|---|---|---|---|---|---|---|---|
| POTASSIUM ALGINATE K-1G | 100~200 (1% AQUEOUS SOLUTION) | 7 | 7 | 7 | 9 | 8 | | |
| SODIUM ALGINATE ULV-L3G | 20~50 (10% AQUEOUS SOLUTION) | | | | | | 5 | 4 |
| POTASSIUM ALGINATE K-ULV-L3G | 20~50 (10% AQUEOUS SOLUTION) | 8 | 7 | 6 | 6 | 6 | | |
| SODIUM ALGINATE I-3G | 300~400 (1% AQUEOUS SOLUTION) | | | | | | 7 | 7 |
| TOTAL ALGINATE | | 15 | 14 | 13 | 15 | 14 | 12 | 11 |
| DISTILLED WATER | | 84.8 | 85.8 | 86.8 | 84.8 | 85.8 | 87.8 | 88.8 |
| SODIUM PYROPHOSPHATE | | 0.2 | 0.2 | 0.2 | 0.2 | 0.2 | 0.2 | 0.2 |
| TOTAL | | 100 | 100 | 100 | 100 | 100 | 100 | 100 |
| ADHESIVENESS | | GOOD | EXCELLENT | EXCELLENT | GOOD | GOOD | EXCELLENT | GOOD |
| MIXING PROPERTY WITH CURING MATERIAL PASTE | | EXCELLENT | EXCELLENT | EXCELLENT | GOOD | EXCELLENT | GOOD | GOOD |
| CONSISTENCY (mm) | | | 38.5 | 40.1 | | | | |

TABLE 3

| ALGINATE | VISCOSITY (mPa · s) | COMPARATIVE EXAMPLE 1 | 2 | 3 | 4 |
|---|---|---|---|---|---|
| POTASSIUM ALGINATE K-1G | 100~200 (1% AQUEOUS SOLUTION) | 6 | 7 | 8 | 9 |
| SODIUM ALGINATE ULV-L3G | 20~50 (10% AQUEOUS SOLUTION) | | | | |
| POTASSIUM ALGINATE K-ULV-L3G | 20~50 (10% AQUEOUS SOLUTION) | | | | |
| SODIUM ALGINATE I-3G | 300~400 (1% AQUEOUS SOLUTION) | | | | |
| TOTAL ALGINATE | | 6 | 7 | 8 | 9 |
| DISTILLED WATER | | 93.8 | 92.8 | 91.8 | 90.8 |
| SODIUM PYROPHOSPHATE | | 0.2 | 0.2 | 0.2 | 0.2 |
| TOTAL | | 100 | 100 | 100 | 100 |
| ADHESIVENESS | | POOR | POOR | POOR | POOR |
| MIXING PROPERTY WITH CURING MATERIAL PASTE | | GOOD | EXCELLENT | EXCELLENT | GOOD |
| CONSISTENCY (mm) | | | 40.8 | 40.3 | |

From Tables 1 to 3, it can be seen that all the test pieces in Examples 1 to 13, in which the viscosity of 10% aqueous solution of the alginate contained in the base material paste at 20° C. is 5 mPa·s or more and 90 mPa·s or less, exhibited favorable adhesiveness and mixing property with the curing material paste. Further, the test pieces (Examples 1, 2, 8, 9) exhibited favorable consistency.

In contrast, when the base material paste does not contain an alginate in which the viscosity of 10% aqueous solution at 20° C. is 5 mPa·s or more and 90 mPa·s or less (Comparative Examples 1 to 4), the test pieces exhibited poor adhesiveness.

The embodiments disclosed above include, for example, the following aspects.

<1> A dental impression material including:

a base material paste that includes an alginate and water; and a curing material paste that includes a gelling reagent and a poorly water-soluble liquid compound, wherein a viscosity of 10% aqueous solution of the alginate at 20° C. is 5 mPa·s or more and 90 mPa·s or less.

<2> The dental impression material according to <1>, wherein a viscosity of 1% aqueous solution of the alginate at 20° C. is 2 mPa·s or less.

<3> The dental impression material according to <1> or <2>, wherein the dental impression material is used for a combined impression.

<4> A combined impression material including:

the dental impression material of any one of <1> to <3>; and an alginate impression material different from the dental impression material.

Although the embodiments of the present invention have been described above, the present invention is not limited to the specific embodiments, and various modifications and changes can be made within the scope of the invention described in the claims.

What is claimed is:

1. A combined dental impression material comprising:

a base material paste that includes a first alginate, a second alginate and water; and a curing material paste that includes a gelling reagent and a liquid compound, wherein the liquid compound has a solubility of 5 grams or less in 100 g of water at 20° C.

a viscosity of 10 mass % aqueous solution of the first alginate at 20° C. is 5 mPa·s or more and 90 mPa·s or less and a viscosity of 1 mass % aqueous solution of the first alginate at 20° C. is 0.1 mPa·s or more and 2 mPa·s or less, and wherein a viscosity of 1 mass % aqueous solution of the second alginate at 20° C. is 100 mPa·s or more and 400 mPa·s or less.

* * * * *